US009486395B2

(12) United States Patent
Lombardo et al.

(10) Patent No.: US 9,486,395 B2
(45) Date of Patent: Nov. 8, 2016

(54) SYNTHETIC SPILANTHOL AND USE THEREOF

(71) Applicant: Takasago International Corporation, Tokyo (JP)

(72) Inventors: Louis Lombardo, Rockleigh, NJ (US); Michael E. Lankin, Rockleigh, NJ (US); Kenya Ishida, Kanagawa (JP); Shigeru Tanaka, Kanagawa (JP); Hideo Ujihara, Kanagawa (JP); Kenji Yagi, Kanagawa (JP); Jennifer B. Tartaglia, Rockleigh, NJ (US); Carter B. Green, Rockleigh, NJ (US); Amrit S. Mankoo, Rockleigh, NJ (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 178 days.

(21) Appl. No.: 14/257,755

(22) Filed: Apr. 21, 2014

(65) Prior Publication Data

US 2014/0227200 A1 Aug. 14, 2014

Related U.S. Application Data

(60) Division of application No. 12/505,283, filed on Jul. 17, 2009, now Pat. No. 8,741,958, which is a continuation-in-part of application No. PCT/JP2009/050566, filed on Jan. 16, 2009.

(60) Provisional application No. 61/174,141, filed on Apr. 30, 2009.

(30) Foreign Application Priority Data

| Jan. 18, 2008 | (JP) | 2008-9295 |
| Jan. 18, 2008 | (JP) | 2008-9821 |
| Jan. 18, 2008 | (JP) | 2008-9832 |
| Jan. 18, 2008 | (JP) | 2008-9851 |

(51) Int. Cl.

| A61K 31/16 | (2006.01) |
| A61K 8/42 | (2006.01) |
| A23L 1/226 | (2006.01) |
| A61Q 5/00 | (2006.01) |
| A61Q 11/00 | (2006.01) |
| A61Q 15/00 | (2006.01) |
| C07C 43/303 | (2006.01) |
| C07C 45/41 | (2006.01) |
| C07C 57/66 | (2006.01) |
| C07C 231/12 | (2006.01) |
| C07C 233/09 | (2006.01) |
| C07C 235/28 | (2006.01) |
| C07C 309/66 | (2006.01) |
| C12P 13/02 | (2006.01) |
| A23G 1/32 | (2006.01) |

(Continued)

(52) U.S. Cl.
CPC . *A61K 8/42* (2013.01); *A23G 1/32* (2013.01); *A23G 3/36* (2013.01); *A23G 4/06* (2013.01); *A23L 1/22614* (2013.01); *A61Q 5/00* (2013.01); *A61Q 11/00* (2013.01); *A61Q 15/00* (2013.01); *C07C 43/303* (2013.01); *C07C 45/41* (2013.01); *C07C 57/66* (2013.01); *C07C 231/12* (2013.01); *C07C 233/09* (2013.01); *C07C 235/28* (2013.01); *C07C 309/66* (2013.01); *C12P 13/02* (2013.01)

(58) Field of Classification Search
CPC ..................................................... A61K 31/16
See application file for complete search history.

(56) References Cited

U.S. PATENT DOCUMENTS

| 3,720,762 A | 3/1973 | Hatasa et al. |
| 4,639,368 A | 1/1987 | Niazi et al. |
| 4,820,506 A | 4/1989 | Kleinberg et al. |

(Continued)

FOREIGN PATENT DOCUMENTS

| CN | 1 128 636 | 8/1996 |
| EP | 0 446 170 | 9/1991 |

(Continued)

OTHER PUBLICATIONS

U.S. Appl. No. 12/505,283, Apr. 22, 2014 Issue Fee payment.

(Continued)

*Primary Examiner* — Jeffrey S Lundgren
*Assistant Examiner* — Chris Simmons
(74) *Attorney, Agent, or Firm* — Baker Botts L.L.P.

(57) ABSTRACT

The present application provides a synthetic spilanthol flavor composition that includes (2E,6Z,8E)-N-(2-methylpropyl)-2,6,8-decatrienamide. The synthetic spilanthol composition can also contain, and at least one of (2E,6E,8E)-N-(2-methylpropyl)-2,6,8-decatrienamide and (2E,6Z,8Z)—N-(2-methylpropyl)-2,6,8-decatrienamide, the (N-(2-methylpropyl)-2,6,8-decatrienamide being present in amounts effective to impart a salivating or tingle effect while reducing the perception of off notes, as compared to the off-notes perceived upon consumption of natural spilanthol (e.g. spilanthol obtained from jambu oleoresin). Methods of increasing salivation and/or providing a tingling sensation upon consuming an orally consumable product that include adding to the product a synthetic spilanthol flavor composition are also provided. Synthetic spilanthol flavor compositions can be added to orally consumed products, such as, but not limited to, foods, beverages, pharmaceuticals, nutraceuticals, or therapeutic compositions, oral personal care products, gums (e.g. chewing gum or bubble gum), candy or lozenges.

9 Claims, No Drawings

(51) Int. Cl.
A23G 3/36 (2006.01)
A23G 4/06 (2006.01)

(56) References Cited

U.S. PATENT DOCUMENTS

| | | |
|---|---|---|
| 4,983,378 A | 1/1991 | Parnell |
| 5,372,834 A | 12/1994 | Buckholz et al. |
| 5,545,424 A | 8/1996 | Nakatsu et al. |
| 6,746,697 B2 | 6/2004 | Wolfson |
| 6,890,567 B2 | 5/2005 | Nakatsu et al. |
| 7,041,311 B2 | 5/2006 | Grainger |
| 8,435,542 B2 | 5/2013 | Manley et al. |
| 8,741,958 B2 | 6/2014 | Lombardo et al. |
| 2003/0035833 A1 | 2/2003 | He |
| 2003/0118628 A1 | 6/2003 | Tutuncu et al. |
| 2003/0215532 A1 | 11/2003 | Nakatsu et al. |
| 2004/0170576 A1 | 9/2004 | Grainger et al. |
| 2004/0241312 A1 | 12/2004 | Gatfield |
| 2006/0024246 A1 | 2/2006 | Maitra et al. |
| 2006/0029665 A1 | 2/2006 | Singh |
| 2007/0202188 A1 | 8/2007 | Ley et al. |
| 2009/0155445 A1 | 6/2009 | Le et al. |
| 2010/0184863 A1 | 7/2010 | Lombardo et al. |
| 2011/0105773 A1 | 5/2011 | Tanaka et al. |
| 2012/0040057 A1 | 2/2012 | Ferri et al. |
| 2012/0129953 A1 | 5/2012 | Le et al. |
| 2014/0099391 A1 | 4/2014 | Manley et al. |

FOREIGN PATENT DOCUMENTS

| | | |
|---|---|---|
| JP | 57-118518 | 7/1982 |
| WO | WO 2004/043906 | 5/2004 |
| WO | WO 2005/011811 | 2/2005 |
| WO | WO 2005/044778 | 5/2005 |
| WO | WO 2005/099473 | 10/2005 |

OTHER PUBLICATIONS

U.S. Appl. No. 12/505,283, Apr. 2, 2014 Notice of Allowance.
U.S. Appl. No. 12/505,283, Dec. 5, 2012 Response to Non-Final Office Action.
U.S. Appl. No. 12/505,283, Jun. 5, 2012 Non-Final Office Action.
U.S. Appl. No. 12/505,283, Dec. 20, 2011 Response to Restriction Requirement.
U.S. Appl. No. 12/505,283, Nov. 28, 2011 Restriction Requirement.
U.S. Appl. No. 11/638,110, Apr. 4, 2013 Issue Fee payment.
U.S. Appl. No. 11/638,110, Jan. 4, 2013 Notice of Allowance.
U.S. Appl. No. 11/638,110, Oct. 24, 2012 Response to Non-Final Office Action.
U.S. Appl. No. 11/638,110, Apr. 24, 2012 Non-Final Office Action.
U.S. Appl. No. 11/638,110, Apr. 6, 2012 Applicant Initiated Interview Summary.
U.S. Appl. No. 11/638,110, Mar. 22, 2012 Restriction Requirement.
U.S. Appl. No. 11/638,110, Jan. 13, 2012 Applicant Initiated Interview Summary.
U.S. Appl. No. 11/638,110, Nov. 17, 2011 Restriction Requirement.
U.S. Appl. No. 11/638,110, Apr. 26, 2011 Amendment and Request for Continued Examination (RCE).
U.S. Appl. No. 11/638,110, Oct. 26, 2010 Final Office Action.
U.S. Appl. No. 11/638,110, Aug. 6, 2010 Response to Notice of Non-Compliant.
U.S. Appl. No. 11/638,110, Jul. 16, 2010 Notice of Non-Compliant.
U.S. Appl. No. 11/638,110, May 10, 2010 Response to Non-Final Office Action.
U.S. Appl. No. 11/638,110, Nov. 10, 2009 Non-Final Office Action.
U.S. Appl. No. 11/638,110, Aug. 21, 2009 Amendment and Request for Continued Examination (RCE).
U.S. Appl. No. 11/638,110, Aug. 17, 2009 Advisory Action.
U.S. Appl. No. 11/638,110, May 8, 2009 Final Office Action.
U.S. Appl. No. 11/638,110, Feb. 3, 2009 Response to Non-Final Office Action.
U.S. Appl. No. 11/638,110, Nov. 3, 2008 Non-Final Office Action.
U.S. Appl. No. 11/638,110, Aug. 11, 2008 Amendment and Request for Continued Examination (RCE).
U.S. Appl. No. 11/638,110, Jan. 11, 2008 Notice of Appeal.
U.S. Appl. No. 11/638,110, Jul. 11, 2007 Final Office Action.
U.S. Appl. No. 11/638,110, May 9, 2007 Response to Non-Final Office Action.
U.S. Appl. No. 11/638,110, Jan. 9, 2007 Non-Final Office Action.
U.S. Appl. No. 11/638,110, Nov. 9, 2006 Response to Restriction Requirement.
U.S. Appl. No. 11/638,110, Sep. 26, 2006 Restriction Requirement.
International Search Report and Written Opinion for PCT/US2006/008016, dated Nov. 29, 2006.
Kaneuchi, et al., "Production of Succinic Acid from Citric Acid and Related Acids by *Lactobacillys* Strains", *Applied and Environmental Microbiology*, 54(12):3053-3056 (1988).
Ley, et al., "Structure Activity Relationships of Trigeminal Effects for Artificial and Naturally Occuring Alkamides related to Spilanthol", *11th Weurmann Flavour Researchn Symposium*, Roskild, Denmark, Jun. 21-24, 2005, 4 pages.
Ramsewak, et al., "Bioactive *N*-isobutylamides from the flower buds of *Spilanthes acmella*", *Phytochemistry*, 51:729-732 (1999).

SYNTHETIC SPILANTHOL AND USE THEREOF

REFERENCE TO RELATED APPLICATIONS

This application is a divisional of U.S. patent application Ser. No. 12/505,283, filed Jul. 17, 2009, which is a continuation in part of International Application No. PCT/JP2009/ 50566, filed Jan. 16, 2009, which claims the benefit of Japanese Application Nos. 2008-9295, 2008-9832, 2008-9851 and 2008-9821, each filed Jan. 18, 2008. U.S. patent application Ser. No. 12/505,283 also claims the benefit of U.S. Provisional Application No. 61/174,141, filed Apr. 30, 2009. The contents of each of the above-mentioned applications are hereby incorporated by reference in their entirety, and to each of the above-mentioned applications priority is claimed.

FIELD OF THE INVENTION

The present application relates to a synthetic spilanthol flavor composition for an orally consumed product (e.g. a food or beverage) that provides a tingle sensation and/or enhances salivation upon consumption of the orally consumed product while reducing the perception of off-notes.

BACKGROUND OF THE INVENTION

Various plant extracts can be employed in flavor compositions as tingling and/or salivation materials. Oftentimes these extracts contain active ingredients which give the extract itself the tingling, numbing and/or stinging sensation and are used in foods as popular spice and/or herb condiments. For example, jambu oleoresin extract, obtained from a green leafy plant native to Southeast Asia (*Spilanthes acmelia, Oleracea*) contains spilanthol. Other examples of extracts that can employed as tingling ingredients include, but are not limited to, Japanese pepper extract (*Zanthoxylum peperitum*), black pepper extract (*Piper nigrum*), cehinacea extract, northern prickly ash extract, Nepalese spice timur extract, and red pepper oleoresin.

Various types of commercial products incorporate ingredients which impart a sensation to the consumer (e.g. a tingling sensation). These ingredients may be used as flavors in a wide range of products for oral care (such as toothpaste, mouthwash, and the like) and foods and beverages (such as chewing gum, soda and the like).

Commonly the tingling ingredient is spilanthol, which is conventionally extracted from natural sources, such as jambu oleoresin extract (also referred to as jambu oleoresin). Jambu oleoresin is commercially available.

It has been found that jambu oleoresin extract, which contains the active ingredient spilanthol, is also conducive to incorporation into a cocktail of sensation invoking materials for a variety of flavor and fragrance applications. Examples are detailed in U.S. Pat. No. 6,780,443 which is herein incorporated by reference.

It has also been found that compositions comprising a tingling ingredient promote salivation in products to which they have been added, such as foods and beverages. Examples are detailed in U.S. Published Application No. 2006/0204551 which is herein incorporated by reference in its entirety.

A sufficient level of salivation is important for good oral hygiene and taste sensation. Dry mouth is conducive to the growth of microorganisms that cause halitosis or bad breath. Accordingly, many breath freshening products include formulations that increase saliva flow in the oral cavity. Dry mouth decreases taste sensation and, thus, may decrease the ability to taste and enjoy food and beverages. Increased saliva flow, conversely, promotes taste sensation and, thus, may increase the ability to taste and enjoy foods and beverages.

Natural jambu oleoresin extract containing spilanthol consists of for example, 30-50% (2E, 6Z, 8E)-N-(2-methylpropyl)-2, 6, 8-decatrienamide isomer in the end product, which is standardized in a carrier to avoid fluctuations due to seasonal crop variations. This oleoresin extract possesses an undesirable off-note aroma or off-note taste (e.g., imparting a food or beverage with green or oily notes) upon being consumed. Hence, there remains a need for salivation or tingling component(s) that are effective to increase salivation or tingle perception without negatively affecting the taste of the product to which the component is added.

SUMMARY OF THE INVENTION

The present application is based on the discovery that synthetic forms of spilanthol, provide salivation or tingling effects comparable to naturally obtained spilanthol, while reducing off-notes perceived upon consuming naturally-obtained spilanthol (e.g. spilanthol obtained from jambu oleoresin). In certain embodiments, the synthetic form of spilanthol contains predominately (2E, 6Z, 8E)-N-(2-methylpropyl)-2, 6, 8-decatrienamide isomer, yet also contains non-trace amounts (e.g. above 0.1 wt %) of the (2E, 6E, 8E) and/or (2E, 6Z, 8Z) isomers.

Accordingly, the present application provides synthetic spilanthol flavor compositions that provide a tingling sensation and/or enhance salivation when added to an orally consumed product, while reducing off-notes associated with spilanthol obtained from natural sources (e.g. jambu oleoresin).

In one embodiment, the synthetic spilanthol flavor composition includes high amounts (2E,6Z,8E)-N-(2-methylpropyl)-2,6,8-decatrienamide (e.g. at least 50 wt % of the (2E,6Z,8E) isomer, based on the total amount of N-(2-methylpropyl)-2,6,8-decatrienamide in the spilanthol flavor composition) in which the N-(2-methylpropyl)-2,6,8-decatrienamide is present in amounts effective to impart a salivation and/or tingling effect when orally consumed, while minimizing off-notes that would otherwise be provided by the (2E,6Z,8E)-N-(2-methylpropyl)-2,6,8-decatrienamide isomer obtained from natural sources (e.g. jambu oleoresin).

The present application also provides an exemplary, non-limiting method for chemically synthesizing spilanthol that includes reacting an ethyl butanoate with a leaving group attached to the 4-carbon (e.g. ethyl 4-bromobutanoate) with a Wittig reagent (e.g. triphenylphosphine) to obtain a phosphonium salt, introducing crotonaldehyde to the phosphonium salt in the presence of a solvent (e.g. toluene) to obtain (4Z, 6E)-ethyl octadienoate, reducing the (4Z, 6E)-ethyl octadienoate to obtain (4Z, 6E)-octadienal, reacting the (4Z, 6E)-octadienal with trimethyl phosphonoacetate in the presence of a solvent (e.g. toluene) cooled to below room temperature, warming the admixture and adding an acid (e.g. 4N—HCl) thereto to form an organic layer, and separating out the organic layer and removing the solvent to obtain primarily (2E,6Z,8E)-methyl decatrienoate. Furthermore, a base (e.g. potassium hydroxide) is then added to the (2E,6Z,8E)-methyl decatrienoate while heating the admixture to above room temperature, followed by cooling this admixture and adding an acid thereto to form (2E, 6Z, 8E)

decatrienoic acid, which is then cooled and to which is added a polar aprotic solvent (e.g. dimethylformamide) to obtain (2E, 6Z, 8E) decatrienoic acid and cooling to below room temperature, and subsequently adding thionyl chloride to obtain (2E, 6Z,8E) decatrienoyl chloride. Following, isobutylamine and base were added to acid chloride to obtain amide, then water is then added to the admixture and spilanthol is separated from the organic layer formed thereby. Products produced by this process may be used as spilanthol flavor compositions.

DETAILED DESCRIPTION

Spilanthol exists as one of the natural constituents contained in plants, and may be isolated from plants by solvent extraction techniques. Such naturally obtained spilanthol consists of the (2E, 6Z, 8E)-N-(2-methylpropyl)-2, 6, 8-decatrienamide isomer, with other olefin isomers (such as the (2E, 6E, 8E) and (2E, 6Z, 8Z) isomers) only present in insignificant, trace amounts (<0.1%). Additionally, spilanthol may be obtained by chemical synthesis. The use of spilanthol resulting from chemical synthesis has been found to be preferred in the present application, as compared to spilanthol extracted from natural sources.

As used herein, the term "natural spilanthol" or "naturally obtained spilanthol" refers to (2E, 6Z, 8E)-N-(2-methylpropyl)-2,6,8-decatrienamide extracted with n-hexane from the aerial part of S. oleracea, by the technique as described on p. 2253 of Chemical Pharm. Bull. 28(7)2251-2253 (1980) under the heading "Extraction and Isolation of Spilanthol," which is hereby incorporated by reference in its entirety. Natural spilanthol contains only trace amounts, if any, of other isomeric forms of N-(2-methylpropyl)-2, 6, 8-decatrienamide besides (2E, 6Z, 8E)-N-(2-methylpropyl)-2,6,8-decatrienamide.

The term "synthetic spilanthol" refers to all isomers of N-(2-methylpropyl)-2, 6, 8-decatrienamide that are produced by a synthetic process, including processes that yield high amounts (e.g. at least 50 wt %. or at least 70 wt %) of (2E, 6Z, 8E)-N-(2-methylpropyl)-2, 6, 8-decatrienamide. In certain embodiments, synthetic spilanthol also contains (2E, 6E, 8E)-N-(2-methylpropyl)-2, 6, 8-decatrienamide and/or (2E, 6Z, 8Z)—N-(2-methylpropyl)-2, 6, 8-decatrienamide isomers.

As used herein, the term "substantially pure N-(2-methylpropyl)-2,6,8-decatrienamide" refers to N-(2-methylpropyl)-2,6,8-decatrienamide prepared by a synthetic method, in any geometrical isomer, which lacks one or more impurities that would impart an off-note (e.g. a green or oily note) upon consumption, as evaluated by a person of ordinary skill in the art. As noted above, such impurities are inevitably present in natural spilanthol, as defined above (e.g. impurities present in spilanthol obtained from jambu oleoresin).

It has been found that the salivation and/or tingling effect of synthetic spilanthol obtained from chemical synthesis, such as the chemical synthesis techniques disclosed or incorporated by reference herein, is superior to that of "natural" spilanthol, such as natural spilanthol obtained from jambu oleoresin. The synthetic spilanthol resulting from chemical synthesis, including, but not limited to, synthetic spilanthol prepared by synthesis techniques disclosed herein, possesses the salivation and/or tingling effect attributes and also maintains the appealing taste of the food or beverage to which the synthetic spilanthol is added. Unless specified otherwise, the term synthetic spilanthol refers to synthetic spilanthol prepared by any technique, including synthesis techniques in addition to those disclosed herein.

This is noteworthy considering that natural spilanthol contained in jambu oleoresin affords similar salivation and/or tingling properties but which color is commonly undesirable browny color, and causes an undesirable off-note or taste (e.g., imparting to a food or beverage green or oily notes). While not being bound by any particular theory, it is believed that synthetically obtained spilanthol including synthetic spilanthol compositions which contains a high amount of the (2E, 6Z, 8E) isomer is almost colorless clear oil and provides a "cleaner" taste since it lacks various impurities that are inevitably present in natural spilanthol that remain after the extraction or isolation step, such as impurities remaining in spilanthol obtained from jambu oleoresin that remain despite the extraction step.

An example embodiment, the compositions of spilanthol are used in chewing gums and confectionaries. Chewing gum compositions include one or more of gum base and most of the other typical chewing gum composition components such as flavoring agents, softeners, sweeteners and the like.

The ingredients used in chewing gum compositions include sweeteners, both natural and artificial and both sugar and sugarless. Sweeteners are typically present in the chewing gum compositions in amounts of from about 20% to 80% by weight, preferably from about 30% to 60% by weight, based on the total weight of the chewing gum composition. Sugarless sweeteners include, but are not limited sugar alcohols such as Sorbitol, manifold, xylitol, hydrogenated starch hydrolysates, maltitol and the like may also be present. High intensity sweeteners such as sucralose, aspartame, neotame, salts of acesulfame, and the like are typically present up to about 1.0% by weight.

Flavoring agents, which can vary over a wide range, may be selected in amounts from about 0.1% to 10.0% by weight, preferably from about 0.5% to 5.0% by weight, based on the total weight of the orally consumed product composition (e.g. the entire weight of the chewing gum composition). Flavoring agents for use in chewing gum compositions are well known and include natural flavors such as citrus oils, peppermint oil, spearmint oil, oil of wintergreen, natural menthol, cinnamon, ginger and the like; artificial flavors such as menthol, carvone, limonene, cinnamic aldehyde, linalool, geraniol, ethyl butyrate, and the like.

An example of the orally consumable products of the invention include mouthwash which is prepared by dissolving synthetic spilanthol and, a flavor such as menthol in water containing a surfactant and then mixing the resulting solution with an aqueous erythritol solution.

Certain embodiments of the present application provide a salivation and/or tingling sensation composition that includes the (2E, 6Z, 8E)-N-(2-methylpropyl)-2, 6, 8-decatrienamide isomer in an amount, based on the total amount of N-(2-methylpropyl)-2, 6, 8-decatrienamide present in the composition, from about 55 wt % to about 95 wt %, or from about 60 wt % to about 90 wt %, or from about 65 wt % to about 85 wt %, or from about 70 wt % to about 80 wt % (e.g. 75 wt %). In certain embodiments, the amount of the (2E, 6E, 8E)-N-(2-methylpropyl)-2,6,8-decatrienamide isomer, based on the total amount of N-(2-methylpropyl)-2, 6, 8-decatrienamide present in the composition, ranges from about 1 wt % to about 40 wt %, or from about 5 wt % to about 30 wt %, or from about 7.5 wt % to about 20 wt %, or from about 10 wt % to about 15 wt % (e.g. 12.5 wt %); and/or the amount of the (2E, 6Z, 8Z)—N-(2-methylpropyl)-

2,6,8-decatrienamide isomer, based on the total amount of N-(2-methylpropyl)-2, 6, 8-decatrienamide present in the composition, ranges from about 1 wt % to about 40 wt %, or from about 5 wt % to about 30 wt %, or from about 7.5 wt % to about 20 wt %, or from about 10 wt % to about 15 wt % (e.g. 12.5 wt %). Preferably, the composition contains both the (2E, 6E, 8E) and (2E, 6Z, 8Z) isomers, in addition to the (2E, 6Z, 8E) isomer.

In certain embodiments, the amount of the (2E, 6E, 8E) and/or (2E, 6Z, 8Z) isomer(s) is not restricted so long as the resulting composition provides a total amount of N-(2-methylpropyl)-2,6,8-decatrienamide (in any geometrical isomer) effective to impart a salivating or tingle effect while reducing off-notes when orally consumed, as compared to the off-notes provided by natural spilanthol compositions (e.g. spilanthol obtained from jambe oleoresin). Reduction of off-notes can be determined, for example, based on hedonic valuation of off-notes by persons of ordinary skill in the art (see, e.g., Examples 9 and 10, supra). As used herein, the term "off-notes" refers to an unpleasant taste and/or after taste that develops over time after consumption of consumables.

The total amount of spilanthol in an orally consumable product can vary widely depending on the amount of the product used at one time and the manner in which it is used or applied, and may be determined by a person of ordinary skill in the art based on, for example, hedonic evaluation. In certain non-limiting embodiments of the present application, the total amount of spilanthol may be from about 0.00001 wt % to 20 wt %, or from about 0.0001 wt % to about 10 wt %, or from about 0.00025 wt % or 0.005 wt % to about 0.1 wt % or 5 wt %, based on the weight of the entire product composition (w/w).

The present invention will be described in detail by the exemplary chemical synthesis described below involving Wittig reactions, however, it should be noted the invention is not limited to this synthesis technique. Additional examples are detailed in PCT Pat, Appl. No. PCT/JP2009/50566, filed Jan. 16, 2009, which is herein incorporated by reference in its entirety.

Chemical Synthesis of Spilanthol

N-(2-methylpropyl)-2,6,8-decatrienamide can be prepared by following chemical steps (CI)~(CIV):

(CI) (Wittig Reaction)

(4Z, 6E)-octadienoate represented by a formula (C3) can be prepared by reacting a phosphonium salt represented by a formula (C2) with crotonaldehyde under basic conditions:

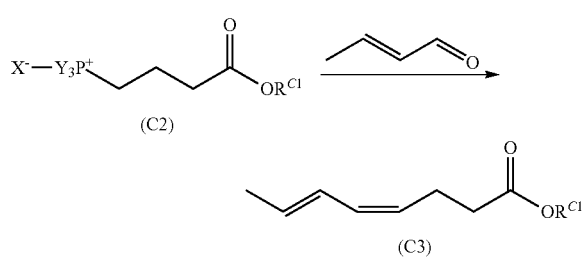

wherein $R^{C1}$ represents an alkyl group having 1 to 4 carbon atoms, X represents a halogen (e.g., a chlorine atom or bromine atom), Y represents an alkyl group or an aryl group which may have a substituent.

(CII) (Reduction)

(4Z,6E)-octadienal (C4) can be prepared by reduction of (4Z,6E)-octadienoate represented by the formula (C3);

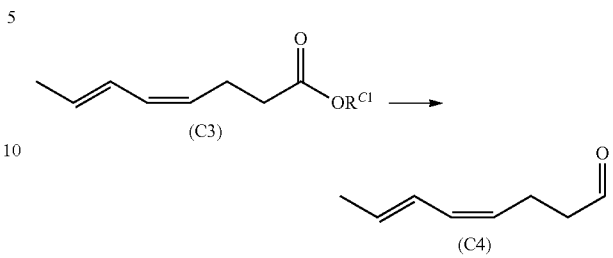

wherein $R^{C1}$ is the same described above.

(CIII) (Wittig Reaction)

(2E,6Z,8E)-decatrienoate represented by a formula (C6) can be prepared by reacting a phosphonophosphate represented by a formula (C5) with (4Z,6E)-octadienal (C4) under basic conditions;

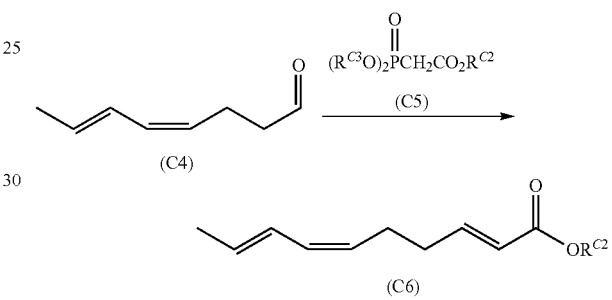

wherein $R^{C2}$ and $R^{C3}$ represent an alkyl group having 1 to 4 carbon atoms)

(CIV) (Amidation)

(2E,6Z,8E)-N-(2-methylpropyl)-2,6,8-decatrienamide is prepared by reacting with decatrienoate represented by the formula (C6) with isobutylamine in the presence of a catalyst, or by a hydrolysed decatrienoate conversion to an acid halide, then reacting the acid halide with isobutylamine;

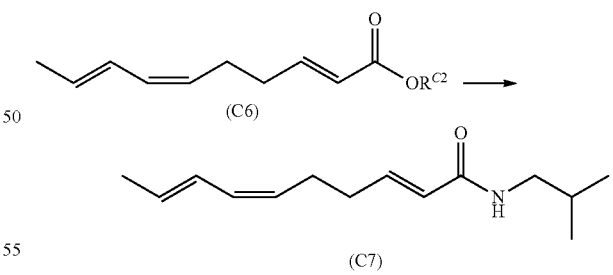

wherein $R^{C2}$ is the same described above.

Other techniques of synthesizing spilanthol known to one of ordinary skill in the art may be used to prepare spilanthol compositions. Any such technique may be employed so long as the particular synthesis techniques will yield (2E,6Z,8E)-N-(2-methylpropyl)-2,6,8-decatrienamide, in which the total amount of N-(2-methylpropyl)-2,6,8-decatrienamide (including all optical isomers) is present in an amount effective to impart a salivation or tingle effect when orally consumed, while reducing the perception of off-notes, as compared to the off-notes perceived upon consumption of natural spilanthol. In certain embodiments, a spilanthol synthesis technique is employed that yields predominately the (2E, 6Z, 8E) isomer, yet non-trace amounts (e.g. above 0.1 wt %) of the (2E,6E,8E) and/or (2E,6E,8Z) isomers.

A person of ordinary skill in the art may resolve by known methods the spilanthol obtained by such synthesis techniques to determine if sufficient amounts of the (2E,6E,8E) and/or (2E,6E,8Z) isomers are synthesized. Such techniques include, for example, formation and recrystallization of diastereomeric salts, separation by gas chromatography or HPLC separation utilizing achiral or chiral stationery phases, diastereomeric crystallization, enzymatic resolution of derivatives, or separation by simulated moving bed (SMB) achiral or chiral chromatography. Other methods that can be used to separate mixtures, include, fractionated crystallization, chromatography and other methods. See, generally, for example, Roger A Sheldon, Chirotechnology: industrial synthesis of optically active compounds, New York, Marcel Dekker, 1993; Principles of Asymmetric Synthesis (Tetrahedron Organic Chemistry), R. E. Gawley et al., Elsevier Science Ltd. (first edition, 1996), each of which are hereby incorporated by reference in their entirety. Characterization and identification of the separated isomers can also be routinely accomplished, for example, with mass spectrometry (including GC-MS), 1H- and 13C-NMR techniques.

Compositions of Spilanthol

In preferred embodiments, the present invention provides tingle and/or salivation compositions comprising synthetic spilanthol that are included in a food, beverage, pharmaceutical, nutraceutical, or therapeutic composition, oral personal care product, gum (e.g. chewing gum or bubble gum), candy or lozenge. The components can be combined and then added to the food or beverage, or the components can be added separately to the food or beverage.

In one embodiment of the present invention, the tingle and/or salivation composition is added to pharmaceutical dosage forms (e.g., a tablet, capsule, drops or lozenges) which contain a therapeutically active agent (e.g. a medicament). For example, one embodiment of the present invention provides a cough drop or lozenge containing a) menthol or other medicaments for the treatment of sore throat, coughing or other upper respiratory ailments and b) synthetic spilanthol (e.g. synthetic spilanthol that contains non-trace amounts of one or more of the (2E,6E,8E) and (2E, 6Z,8Z) isomers).

The synthetic spilanthol described herein can be added to, for example, compositions for the preparation of carbonated or non-carbonated fruit beverages, carbonated cola drinks, wine coolers, fruit liquors, cordials, milk drinks, flavored water, powders for drinks (e.g., powdered sports or "hydrating" drinks), frozen confectionery such as ice creams, sherbets, and ice-lolly, hard candy, soft candy, taffy, chocolates, sugarless candies, desserts such as jelly and pudding; confectionery such as cakes, cookies, chewing gum, bubble gum, condiments, spices and seasonings, dry cereal, oatmeal, granola bars, alcoholic beverages, energy beverages, juices, teas, coffees, salsa, gel beads, film strips for halitosis, gelatin candies, pectin candies, starch candies, lozenges, cough drops, throat lozenges, throat sprays, toothpastes and mouth rinses.

The synthetic spilanthol compositions may also be added to, for example, Japanese confectionery such as buns with bean-jam filling, bars of sweet jellied bean paste, sweet jellied pounded rice; jams; candies; breads; tea beverages and favorite beverages such as green tea, oolong tea, black tea, persimmon leaf tea, Chamomile tea, Sasa veitchii tea, mulberry leaf tea, Houttuynia cordata tea, Puer tea, Mate tea, Rooibos tea, Gimunema tea, Guava tea, coffee, espresso, and hot and cold espresso and coffee products obtained by mixing espresso and/or coffee with milk, water or other liquids suitable for oral consumption (e.g. lattes, cafe au lait, cafe mocha) and cocoa; soups such as Japanese flavor soup, western flavor soup, and Chinese flavor soup; seasonings; various instant beverages and foods; various snack foods; compositions for oral use and the like.

The synthetic spilanthol compositions can also be added to, for example, fragrance products, perfume, eau de perfume, eau de toilet, eau de cologne, and the like; skin-care cosmetics, face washing creams, varnishing creams, cleansing creams, cold creams, massage creams, milky lotions, skin toning lotion, cosmetic solution, packs, makeup remover, and the like; as makeup cosmetics, foundations, face powders, pressed powders, talcum powders, lip sticks, lip creams, cheek powders, eyeliners, mascara, eye shadows, eyebrow pencils, eye packs, nail enamels, nail enamel removers, and the like; as hair care cosmetics, pomades, brilliantine, setting lotions, hair sticks, hair solids, hair oils, hair treatments, hair creams, hair tonics, hair liquids, hair sprays, hair restorers, hair dyes, and the like; as sunburn cosmetics, suntan products, sunscreen products, and the like; as medical cosmetics, antiperspirants, after-shave lotions and gels, permanent wave lotion, medicated soaps, medicated shampoos, medicated skin care products, and the like; as hair care products, shampoos, rinses, shampoo-including-rinse, hair conditioners, hair treatments, hair packs, and the like; as soaps, toilet soaps, bath soaps, perfumed soaps, transparent soaps, synthetic soaps, and the like; as body washing soaps, body soaps, body shampoos, hand soaps, and the like; as agents for bathing, bathing agents (e.g. bath salts, bath tablets, bath liquids, and the like), foam bath (bubble bath and the like), bath oils (e.g. bath perfumes, bath capsules and the like), milk bath, bath gel, bath cubes, and the like; as detergents, heavy duty detergents for clothes, light duty detergents for clothes, liquid detergents, laundering soaps, compact detergents, powder soaps, and the like; as softening finishing agents, softeners, furniture care, and the like; deodorants, aromatic substance; repellent; as the compositions for oral care, tooth pastes, mouth cleaners, mouth wash, troches, chewing gums, and the like; and as pharmaceutical products, poultices, external skin care pharmaceuticals such as ointments, internal administration medicines, and the like.

As disclosed in U.S. Pat. No. 6,780,443, which is hereby incorporated by reference, spilanthol can be combined with a cooling sensate and/or a waning or pungent sensate to provide an immediate effect on the user. Accordingly, synthetic spilanthol of the present application can be combined with one or more of a cooling sensate or warming sensate and added to the end product.

Examples of the warming and/or pungent substances that can be combined with synthetic spilanthol include, but are not limited to, vanillyl ethyl ether, vanillyl propyl ether, vanillyl butyl ether, vanillin propylene glycol acetal, vanillin-1,2-hexylene glycol acetal, vanillin-1,2-butylene glycol acetal, vanilli-1-butoxyglycerol acetal, ethylvanillin propylene glycol acetal, capsaicin, gingerol, cayenne pepper oil, cayenne pepper oleoresin, ginger oleoresin, nonylic acid vanillylamide, jambu oleoresin, zanthoxylum extract, sanshool I, sanshool II, zanthoxylum armatamide, black pepper extract, chavicine, piperine, vanillyl pentyl ether, vanillyl hexyl ether, vanillyl butyl ether acetate, 4-(1-menthoxymethyl)-2-phenyl-1,3-dioxolan, 4-(1-menthoxymethyl)-2-(3',4'-dihydroxyphenyl)-1,3-dioxolan, 4-(1-menthoxymethyl)-2-(2'-hydroxy-3'-methoxyphenyl)-1,3-dioxolan, 4-(1-menthoxymethyl)-2-(4'-methoxyphenyl)-1,3dioxolan, 4-(1-menthoxymethyl)-2-(3',4'-methylenedioxyphenyl)-1,3-dioxolan, 4-(1-menthoxymethyl)-2-(3'-methoxy-4'-hydroxyphenyl)-1,3-dioxolan, red pepper oil, red pepper oleoresin, ginger oleoresin, and jambu oleoresin.

Examples of cooling sensates that can be combined with synthetic spilanthol include, for example, menthol, menthone, camphor, pulegol, isopulegol, cineole, Japanese mint oil, peppermint oil, spearmint oil, eucalyptus oil, 3-1-menthoxypropane-1,2-diol, N-alkyl-p-menthane-3-carboxamide, 3-1-menthoxy-2-methylpropane-1,2-diol, p-menthane-3,8-diol, 2-1-menthoxyethan-1-ol, 3-1-menthoxypropan-1-ol, menthyl lactate, menthone glycerin ketal, N-methyl-2,2-isopropylmethyl-3-methylbutanamide, menthyl glyoxylate, 1-(2-hydroxy-4-ethylcyclohexyl)-ethanone, (1)-menthyl 3-hydroxybutanoate, (1)-menthyl (3R)-hydroxybutanoate, (1)-menthyl (3S)-hydroxybutanoate, (1)-menthyl lactate, (1)-menthone glycerin ketal, 2-(2-1-menthyloxyethyl)ethanol, menthyl 2-pyrrolidone-5-carboxylate, monomenthyl succinate, alkali metal salts of monomenthyl succinate, and alkali earth metal salts of monomenthyl succinate, monomenthyl glutarate, alkali metal salts of monomenthyl glutarate, alkali earth metal salts of monomenthyl glutarate, N-[[5-methyl-2-(1-methylethyl)cyclohexyl]carbonyl]glycine, p-menthane-3-carboxylic acid glycerol ester, (I)-menthol propylene glycol carbonate; Menthol ethylene glycol carbonate, N-(2-(Pyridin-2-yl)ethyl)-3-p-menthanecarboxamide, N-(4-cyanomethylphenyl)-p-menthanecarboxamide and 6-isopropyl-3,9-dimethyl-1,4-dioxaspiro[4.5]decan-2-one.

As disclosed in U.S. Published Application No. 2006/0204551, which is hereby incorporated by reference, the combination of spilanthol and a food acid provides an increased salivation effect. Accordingly, synthetic spilanthol of the present application can be combined with one or more food acids and added to the end product. In one embodiment, the food acid to be combined with synthetic spilanthol is selected from acetic acid, adipic acid, aspartic acid, benzoic acid, caffeotannic acid, citric acid, iso-citric acid, citramalic acid, formic acid, fumaric acid, galacturonic acid, glucuronic acid, glyceric acid, glycolic acid, ketoglutaric acid, α-ketoglutaric acid, lactic acid, lactoisocitric acid, malic acid, oxalacetic acid, oxalic acid, pyruvic acid, quinic acid, shikimic acid, succinic acid, tannic acid, and tartaric acid The use levels of synthetic spilanthol in various compositions may be adjusted by persons of ordinary skill in the art depending on the flavor of other additives employed in the end use food or beverage, or the taste or flavor of the food or beverage itself. In certain embodiments, the amount of synthetic spilanthol is preferably about 0.00001 to 30% by weight and more preferably 0.0001 to 10% by weight, based on the total weight of the end product.

In certain embodiments, the synthetic spilanthol of the present application is included in along with a carrier solvent. Carrier solvents that can be used include, but are not limited to propylene glycol and medium-chain triglycerides. As known to those skilled in the art, propylene glycol can be used for water soluble flavors, and medium-chain trigylcerides can be employed with oil soluble flavors.

EXAMPLES

The following examples illustrate the invention without limitation.

Example 1

(a) First Wittig Reaction

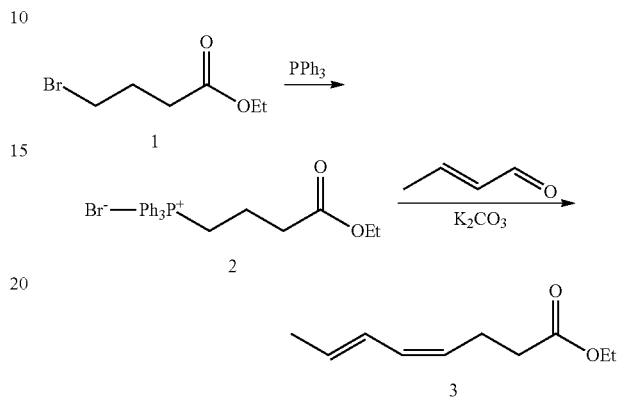

Under a nitrogen atmosphere, ethyl 4-bromobutanoate (1) (195 g, 1.0 mol), triphenylphosphine (288 g, 1.1 mol), and acetonitrile (195 ml) were placed into a 1 L flask, and stirred at 90° C. for 40 hours. Then, the reaction mixture was added drowsier to toluene (800 ml), the mixture was cooled to 20° C. and precipitation was collected by filtration and dried in vacuum (50° C./1 tore) to obtain phosphonium salt (2) (420 g, 0.92 mol, yield: 92%).

Under a nitrogen atmosphere, phosphonium salt (2) (420 g, 0.92 mol), toluene (1600 ml), potassium carbonate (506.2 g, 3.66 mol) and crotonaldehyde (256.7 g, 3.66 mol) were placed into a 5 L flask, and stirred at 65° C. for 7 hours. The reaction mixture was cooled to room temperature, and then water (840 g) was added thereto, the mixture was stirred for 30 minutes, and the organic layer was separated. The obtained organic layer was concentrated in vacuum to obtain a crude product, and this crude product was distilled in vacuum (65-70° C./1.5 tore) to obtain (4Z, 6E)-ethyl octadienoate (3) (114.4 g, 0.68 mol, yield: 74%).

(b) Reduction

Under a nitrogen atmosphere, (4Z, 6E)-ethyl octadienoate (3) (26.9 g, 0.16 mol) and diethylether (250 ml) were placed into a 500 ml flask and cooled to −75° C. DIBAl (1.0 mol/L hexane solution, 195.8 ml, 0.192 mol) was added dropwise thereto within 3 hours, and the mixture was stirred for 30 minutes. Then the reaction mixture was added to cooled (0° C.) 4N—HCl (547 g), the organic layer was separated, and the aqueous layer was extracted with ether (50 ml). The combined organic layer was washed with brine, dried with magnesium sulfate, and concentrated in vacuum to obtain (4Z, 6E)-octadienal (4) (20.0 g, purity: 96%).

(c) Second Wittig Reaction

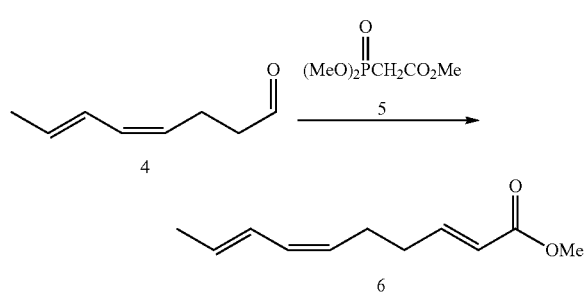

Under a nitrogen atmosphere, sodium hydride (7.37 g, 0.161 mol) and toluene (100 ml) were placed into a 500 ml flask, and the slurry was cooled to 0° C. Then, the mixture of (4Z, 6E)-octadienal (4) 20.0 g) obtained above, trimethyl phosphonoacetate (5) (30.8 g, 0.169 mol) and toluene (200 ml) was added dropwise thereto within 1.5 hours. After a dropwise, the temperature of the reaction mixture was warmed to 25° C., continuing stirring for 4 hours, then 4N—HCl (50 ml) was added thereto. The organic layer was separated, additionally, the aqueous layer was extracted with hexane (50 ml×2). The obtained organic layer was combined, washed with water (2 times), and dried with magnesium sulfate. The solvent of the organic layer was removed, and the residue was distilled in vacuum (75° C./0.5 tore) to obtain (2E, 6Z, 8E)-methyl decatrienoate (6) (19.69 g).

(d) Synthesis of Spilanthol

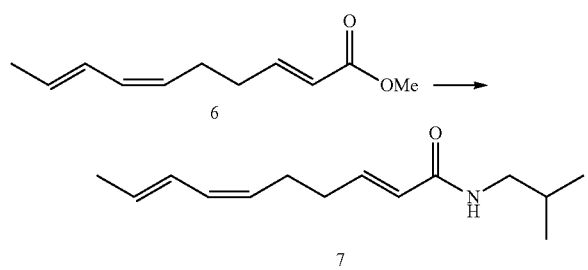

Under a nitrogen atmosphere, (2E, 6Z, 8E)-methyl decatrienoate (6) (19.1 g, GC purity: 82.9%) and 5 mol/L aqueous solution of potassium hydroxide were placed into a 200 ml flask, and the mixture was stirred at 70° C. for 2 hours. The reaction mixture was cooled to room temperature, then 5N—HCl (63 ml, 0.30 mol) was added thereto, and extracted with toluene (32 ml) to obtain (2E, 6Z, 8E)-decatrienoic acid/toluene solution.

Next, under a nitrogen atmosphere, (2E, 6Z, 8E)-decatrienoic acid/toluene solution obtained above and DMF (3.7 g, 0.05 mol) were placed into a 100 ml flask, the mixture was cooled to 5° C. Thionyl chloride (11.9 g, 0.10 mol) was added thereto, and stirred at 5° C. for 0.5 hours to obtain a solution of (2E, 6Z, 8E)-decatrienoyl chloride (8).

Under a nitrogen atmosphere, isobutylamine (7.3 g, 0.10 mol), triethylamine (10.1 g, 0.10 mol) and toluene (32 ml) were placed into a 200 ml flask, the mixture was cooled to 5° C. The toluene solution of (2E, 6Z, 8E)-decatrienoyl chloride (8) obtained above was added thereto, and the mixture was stirred at 5° C. for 0.5 hours. Water was added to the reaction mixture, the organic layer was separated, washed with 5% aqueous solution of sodium carbonate, 0.1 mol/L sodium hydroxide and water. The solvent of the organic layer was evaporated in vacuum, the residue was distilled (130-135° C./0.1 tore) to obtain 19.7 g of spilanthol (7) (GC purity; 78.7%, yield 79% from (6)).

The spilanthol so obtained from chemical synthesis comprises predominately the (2E,6Z,8E)-N-(2-methylpropyl)-2,6,8-decatrienamide isomer and also the isomers (2E,6E,8E)-N-(2-methylpropyl)-2,6,8-decatrienamide and (2E,6Z,8Z)—N-(2-methylpropyl)-2,6,8-decatrienamide.

Example 2

A flavored chewing gum may be prepared from the ingredients shown below:

| Chewing Gum Ingredients | % |
|---|---|
| Chewing gum Base | 97.10 |
| Citric acid | 1.00 |
| Flavor (up to 2.5%) | 2.5 |
| Intensate ® Art Flv Salivation Enhancer (containing 2.5 wt % of synthetic spilanthol) | 0.30 |
| | 100.00 |

Two batches of chewing gum were prepared with two individual flavor variants. A panel of expert evaluators (n=8) rated the chewing gum for "overall liking". The synthetic spilanthol employed in this and the following examples is representative of the product obtained by the synthesis scheme described above.

The scale utilized for this evaluation and all subsequent hedonic evaluations is as follows: Overall Liking: 1—Dislike Extremely, 2—Dislike Very Much, 3—Dislike Moderately, 4—Dislike Slightly, 5—Neither Like nor Dislike, 6—Like Slightly, 7—Like Moderately, 8—Like Very Much, 9—Like Extremely.

The panel's average results are set forth below (1=lowest, 9=highest).

| Flavor Variants | n | Hedonic Score (1-9) |
|---|---|---|
| Strawberry Lime | 8 | 7.6 |
| Cinnamon | 8 | 8.6 |

Example 3

A chewy candy may be prepared from the ingredients shown below:

| Chewy Candy Ingredient | Amount (g) |
|---|---|
| 42 DE Corn Syrup | 500 |
| Sugar | 390 |
| Water | 130 |
| Gelatin | 17.5 |
| Water, Hot (176-194 F) | 35 |
| Sugar | 17.5 |
| Palm Kernel Oil | 45 |
| Lecithin | 3 |
| Powdered Sugar | 26 |
| Acid | up to 1% |
| Flavor | up to 1.2% |
| Intensates ® N&A Tingle Fl OS (containing 2.5 wt % of synthetic spilanthol) | 0.30% |

Four batches of chewy candy containing a tingle flavor were prepared with four individual flavor variants. A panel of expert evaluators (n=6 or 7) rated the chewy candies for "overall liking" using the scale detailed in Example 1. The panel's average results are set forth below (1=lowest, 9=highest).

| Flavor Variants | n | Hedonic Score (1-9) |
|---|---|---|
| Passion fruit Guava | 6 | 7.2 |
| Sour Cherry Lime | 7 | 6.6 |
| Yuzu Melon | 7 | 6.6 |
| Lemon Lime | 7 | 7.1 |

Example 4

A pressed candy may be prepared from the ingredients shown below:

| Ingredients | Weights |
|---|---|
| Sorbitol P60W | 95.45 g |
| Citric Acid | 0.50 g |
| Malic Acid | 0.50 g |
| Sucralose | 0.15 g |
| Magnesium Stearate | 0.80 g |
| Flavor (approx. 2%) | 2.00 g |
| Micron ® Intensate ® Tingle Fl (containing 2.5 wt % of synthetic spilanthol) | 0.60 g |
| Total | 100.00 g |

Two batches of tablet candy were prepared with two individual flavor variants. A panel of expert evaluators (n=7) rated the tablets for "overall liking" using the scale detailed in Example 1. The panel's average results are set forth below (1=lowest, 9=highest),

| Flavor Variants | n | Hedonic Score (1-9) |
|---|---|---|
| Apple | 7 | 8.4 |
| Tropical guava | 7 | 6.8 |

Example 5

A flavored dark chocolate may be prepared by adding the ingredients shown below to molten chocolate:

| Ingredient | Weights |
|---|---|
| Flavor (0.3-0.5) | 0.4 |
| Intensates ® N&A Tingle Fl OS (containing 2.5 wt % of synthetic spilanthol) | 0.3 |

Three batches of flavored dark chocolate were prepared. A panel of expert evaluators (n=7 or 8) rated the dark chocolate for "overall liking" using the scale detailed in Example 1. The panel's average results are set forth below (1=lowest, 9=highest).

| Flavor Variant | n | Hedonic Score (1-9) |
|---|---|---|
| Chili & Cinnamon | 8 | 7.3 |
| Spicy Ginger | 8 | 7.7 |
| Passion fruit Jalapeno | 7 | 8.6 |

Example 6

A hard candy may be prepared from the ingredients shown below:

| Ingredient | Weights |
|---|---|
| sucrose | 79.0 |
| Corn syrup, 42 DE | 19.0 |
| HFCS 55 | 1.0 |
| flavors | 0.6-0.8 |
| Intensates ® N&A Tingle Fl OS (containing 2.5 wt % of synthetic spilanthol) | 0.1 |
| Citric acid | 0.2 |
| Malic acid | 0.2 |

Four batches of flavor containing hard candy were prepared. A panel of expert evaluators (n=7 or 8) rated the flavor containing hard candy for "overall liking" using the scale detailed in Example 1. The panel's average results are set forth below (1=lowest, 9=highest).

| Flavor Variant | n | Hedonic Score (1-9) |
|---|---|---|
| Watermelon | 8 | 7.3 |
| Raspberry | 8 | 7.5 |
| Pineapple | 8 | 6.4 |
| Cherry | 7 | 6.8 |

Example 7

A flavored chewing gum may be prepared from the ingredients shown below:

| Strawberry Lime Chewing Gum | | |
|---|---|---|
| Ingredients | Control | w/salivation |
| Chewing gum Base | 97.4 | 97.10 |
| Citric acid | 1 | 1.00 |
| Art Strawberry Fl OS | 1 | 1.00 |
| Vivid ™ N&A Fl Key Lime type OS | 0.6 | 0.60 |
| Intensate ® Art Flv Salivation Enhancer (containing 0.3 wt % of synthetic spilanthol) | XX | 0.30 |
| | 100.00 | 100.00 |

Two batches of chewing gum were prepared with and without Intensate® Art Flavor Salivation Enhancer flavor containing synthetic spilanthol. A panel of expert evaluators (n=8) rated the tablets for "overall liking" using the scale detailed in Example 1. The panel's average results are set forth below (1=lowest, 9=highest).

| Flavor Variants | n | Hedonic Score (1-9) |
|---|---|---|
| Strawberry Lime | 8 | 7.6 |
| Strawberry Lime without enhancer | 8 | 6.5 |

The chewing gum containing the synthetic spilanthol was preferred.

Example 8

A flavored cough drop lozenge may be prepared from the ingredients shown below:

| Ingredient | Control % | With Salivation Enhancer % |
|---|---|---|
| Berry Mentholyptus Cough Drop Base | 99.82 | 99.73 |
| Intensates ® N&A Cooling Fl OS | 0.18 | 0.18 |
| Intensates ® Art. Fl Salivation Enhancer OS (containing 0.3 wt % of synthetic spilanthol) | XX | 0.09 |

Two batches of lozenges were prepared with and without Intensate® Art Flavor Salivation Enhancer flavor containing synthetic spilanthol. A panel of expert evaluators (n=8) rated the tablets for "overall liking" using the scale detailed in Example 1. The panel's average results are set forth below (1=lowest, 9=highest).

| Flavor Variant | n | Hedonic Score (1-9) |
|---|---|---|
| Strawberry with Salivation enhancer | 8 | 6.3 |
| Strawberry without Salivation enhancer | 8 | 5.8 |

The lozenge containing the enhancer was preferred.

Example 9

Two batches of tropical fruit flavored chewing gum were prepared. The first batch (Batch A) contained 0.78% by weight of tropical fruit flavor. Additionally, the first batch (Batch A) contained 0.30% by weight of Intensate® Artificial Flavor Salivation Enhancer (containing 0.3 wt % of natural spilanthol).

The second batch (Batch B) of chewing gum also contained 0.78% by weight of tropical fruit flavor. Additionally, the second batch (Batch B) contained 0.30% by weight of Intensate® Natural and Artificial Flavor Salivation Enhancer (containing 0.3 wt % of synthetic spilanthol).

Batches A (flavor+Intensate® Natural and Artificial Flavor Salivation Enhancer) and B (flavor+Intensate® Natural and Artificial Flavor Salivation Enhancer) were orally administered to a panel of eight trained evaluators.

The panelists rated the salivation intensity of the sample on a scale of 1-9 at 1, 2, 3 and 4 min after administration ("salivation intensity"). The panelist also rated the flavor off-notes of the sample on a scale of 1 (lowest)-9 (highest) at 1, 2, 3 and 4 min after administration ("off-note intensity").

The panel's average results for the Salivation Intensity and Off-note Intensity are set forth below (1=lowest, 9=highest). The panel's average results for both evaluations are set forth below (1=lowest, 9=highest).

| Time Interval | Salivation Intensity -- Batch A (flavor + Intensate ® Natural and Artificial Flavor Salivation Enhancer with natural spilanthol) | Salivation Intensity -- Batch B (flavor + Intensate ® Natural and Artificial Flavor Salivation Enhancer with synthetic spilanthol) | Flavor Off-notes Batch A | Flavor Off-notes Batch B |
|---|---|---|---|---|
| 1 minute | 6.75 | 6.13 | 2.25 | 1.62 |
| 2 minutes | 5.57 | 5.58 | 2.15 | 1.48 |
| 3 minutes | 4.35 | 4.48 | 1.97 | 1.85 |
| 4 minutes | 4.18 | 4.02 | 2.45 | 1.90 |
| Average over 4 minute test | 5.21 | 5.05 | 2.21 | 1.71 |

The average salivation results of the two samples are comparable. However, the average flavor off-note determination shows a distinct preference for the flavor containing synthetic spilanthol.

Example 10

Two batches of unflavored chewing gum were prepared. The first batch (Batch A) contained 1.00% by weight of an Intensate® Natural and Artificial Tingle Flavor (containing natural spilanthol) and an additional 0.3% citric acid.

The second batch (Batch B) of chewing gum contained 1.00% by weight of an Intensate® Natural and Artificial Tingle Flavor (containing synthetic spilanthol) and an additional 0.3% citric acid.

Batches A (Intensate® Natural and Artificial Tingle Flavor with natural spilanthol) and B (Intensate® Natural and Artificial Tingle Flavor with synthetic spilanthol) were orally administered to a panel of eight trained evaluators.

The panel's average results for the Tingle Intensity Test at the set forth below (1=lowest, 9=highest). The panel's average results for Flavor Off-note Intensity Test at the set forth below (1=lowest, 9=highest).

| Time Interval | Tingle Intensity -- Batch A (Intensate ® Natural and Artificial Tingle Flavor with natural spilanthol) | Tingle Intensity -- Batch B (Intensate ® Natural and Artificial Tingle Flavor with synthetic spilanthol) | Flavor Offnotes Batch A (natural spilanthol) | Flavor Offnotes Batch B (synthetic spilanthol) |
|---|---|---|---|---|
| 1 minute | 1.54 | 1.87 | 2.46 | 1.99 |
| 2 minutes | 2.84 | 3.17 | 2.56 | 2.23 |
| 3 minutes | 3.57 | 3.51 | 2.39 | 2.61 |
| 4 minutes | 3.87 | 3.89 | 2.57 | 2.66 |
| Average over 4 minute test | 2.96 | 3.11 | 2.49 | 2.37 |

The average results of the two samples show that the sample containing synthetic spilanthol delivers a stronger and cleaner tingle performance over the 4 minute evaluation.

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A method of increasing salivation and/or providing a tingling sensation in an oral cavity upon consuming an orally consumable product, while reducing perceived off-notes, comprising administering the orally consumable product to the oral cavity, wherein the orally consumable product comprises a flavor composition comprising synthetic spilanthol, wherein the synthetic spilanthol contains
   (i) from 55% to 95% by weight of (2E,6Z,8E)-N-(2-methylpropyl)-2,6,8-decatrienamide; and
   (ii) one compound selected from the group consisting of (2E,6E,8E)-N-(2-methylpropyl)-2,6,8-decatrienamide, (2E,6Z,8Z)—N-(2-methylpropyl)-2,6,8-decatrienamide, and a combination thereof, and
   wherein each compound is present in an amount of at least 1% by weight based on the total amount of N-(2-methylpropyl)-2,6,8-decatrienamide in the composition.

2. The method of claim 1, wherein the total amount of N-(2-methylpropyl)-2,6,8-decatrienamide is effective to impart a salivation or tingle effect when orally consumed while reducing the perception of off-notes, as compared to the off-notes perceived upon consumption of natural spilanthol.

3. The method of claim 1, wherein the total amount of N-(2-methylpropyl)-2,6,8-decatrienamide is effective to increase salivation when orally consumed.

4. The method of claim 1, wherein the total amount of N-(2-methylpropyl)-2,6,8-decatrienamide is effective to provide a tingling sensation when orally consumed.

5. The method of claim 1, wherein the amount of (2E, 6E, 8E)-N-(2-methylpropyl)-2,6,8-decatrienamide or (2E, 6Z, 8Z)—N-(2-methylpropyl)-2,6,8-decatrienamide is at least 5 wt %, based on the total amount of N-(2-methylpropyl)-2,6,8-decatrienamide present in the composition.

6. The method of claim 1, wherein the amount of (2E,6E,8E)-N-(2-methylpropyl)-2,6,8-decatrienamide or (2E,6Z,8Z)—N-(2-methylpropyl)-2,6,8-decatrienamide is at least 10 wt %, based on the total amount of N-(2-methylpropyl)-2,6,8-decatrienamide present in the composition.

7. The method of claim 1, wherein the flavor composition lacks impurities found in natural spilanthol compositions obtained from jambu oleoresin.

8. The method of claim 1, wherein the orally consumable product is selected from the group consisting of carbonated fruit beverages, sport beverages, carbonated cola drinks, wine coolers, cordials, flavored water, powders for drinks, hard candy, soft candy, taffy, chocolates, sugarless candies, chewing gum, bubble gum, condiments, spices and/or seasonings, dry cereal, oatmeal, granola bars, alcoholic beverages, energy beverages, juices, teas, coffees, salsa, gel beads, film strips for halitosis, gelatin candies, pectin candies, starch candies, lozenges, cough drops, throat lozenges, throat sprays, toothpastes, mouth rinses, and combinations thereof.

9. The method of claim 8, wherein the orally consumable product is selected from the group consisting of chewing gum, bubble gum, and a combination thereof.

* * * * *